United States Patent
Satake (10) Patent No.: US 8,812,267 B2
(45) Date of Patent: Aug. 19, 2014

(54) DEVICE FOR DETECTING CONTAMINATION LEVEL OF OPERATING OIL

(75) Inventor: Hidetoshi Satake, Tsuchiura (JP)

(73) Assignee: Hitachi Construction Machinery Co., Ltd., Tokyo (JP)

( * ) Notice: Subject to any disclaimer, the term of this patent is extended or adjusted under 35 U.S.C. 154(b) by 448 days.

(21) Appl. No.: 13/001,573

(22) PCT Filed: Jun. 26, 2009

(86) PCT No.: PCT/JP2009/061751
§ 371 (c)(1),
(2), (4) Date: Feb. 4, 2011

(87) PCT Pub. No.: WO2009/157550
PCT Pub. Date: Dec. 30, 2009

(65) Prior Publication Data
US 2011/0153275 A1    Jun. 23, 2011

(30) Foreign Application Priority Data

Jun. 27, 2008    (JP) ................................. 2008-168807

(51) Int. Cl.
| | | |
|---|---|---|
| G06F 11/30 | (2006.01) | |
| E02F 9/22 | (2006.01) | |
| F15B 21/04 | (2006.01) | |
| G01N 21/53 | (2006.01) | |
| E02F 9/26 | (2006.01) | |
| E02F 9/08 | (2006.01) | |

(52) U.S. Cl.
CPC .............. *E02F 9/226* (2013.01); *E02F 9/2296* (2013.01); *F15B 21/041* (2013.01); *G01N 21/534* (2013.01); *E02F 9/2285* (2013.01); *E02F 9/26* (2013.01); *E02F 9/0883* (2013.01)
USPC ........ 702/184; 702/33; 137/544; 137/625.65; 184/6.24

(58) Field of Classification Search
USPC .............. 702/183, 184, 33, 182; 73/168, 861; 377/50; 137/544, 625.65; 184/6.24
See application file for complete search history.

(56) References Cited

U.S. PATENT DOCUMENTS 3,968,429 A * 7/1976 Coulter et al. .................. 377/50
(Continued)

FOREIGN PATENT DOCUMENTS

| EP | 0 408 758 A1 | 1/1991 |
|---|---|---|
| JP | 2-170049 A | 6/1990 |

(Continued)

OTHER PUBLICATIONS

Ray Thibault, Oil Cleanliness: The Key to Equipment Reliability, 2007.*
James C. Fitch, Proactive and Predictive Strategies for Setting Oil Analysis Alarms and Limits, 1998.*

(Continued)

*Primary Examiner* — Sujoy Kundu
*Assistant Examiner* — Harun Chowdhury
(74) *Attorney, Agent, or Firm* — Crowell & Moring LLP (57) ABSTRACT

A contamination level determination system for hydraulic oil is provided with a pilot filter arranged in a line of a hydraulic circuit of a hydraulic working machine to remove, from the hydraulic oil, foreign matter of particle sizes that may cause an operation failure of the hydraulic working machine. A first light-blocking sensor senses passage of foreign matter on an upstream side of the pilot filter. A second light-blocking sensor senses passage of foreign matter on a downstream side of the pilot filter. An onboard controller unit functions to determine a frequency of sensing of foreign matter by the first light-blocking sensor, to determine a frequency of sensing of foreign matter by the second light-blocking sensor, and to determine a contamination level on the upstream side of the pilot filter on the basis of results of the determinations from both sensors.

6 Claims, 3 Drawing Sheets

(56) References Cited

U.S. PATENT DOCUMENTS

| | | | |
|---|---|---|---|
| 5,239,861 A | 8/1993 | Fujita et al. | |
| 6,619,112 B2 * | 9/2003 | Juhasz | 73/168 |
| 6,912,479 B2 * | 6/2005 | Ryu et al. | 702/183 |
| 2004/0128107 A1 | 7/2004 | Ryu et al. | |
| 2008/0262650 A1 * | 10/2008 | Dorendorf et al. | 700/240 |

FOREIGN PATENT DOCUMENTS

| | | |
|---|---|---|
| JP | 6-117987 A | 4/1994 |
| JP | 2000-303504 A | 10/2000 |
| JP | 2004-19692 A | 1/2004 |
| JP | 3890036 B2 | 12/2006 |
| JP | 2008-96211 A | 4/2008 |

OTHER PUBLICATIONS

The Micron Rating for Media in Fluid Filters, Filter Manufacturers Council, 2005.*

Barry M. Verdegan, The New NIST Traceable Particle Counter Calibration Standard—Transitioning from ISO 4402 to ISO 11171, International Exposition for Power Transmission and Technical Conference, Apr. 2000.*

International Search Report dated Aug. 4, 2009 including English-language translation (Four (4) pages).

"Condition Monitoring Fuer Hydraulikund Schmierfluessigkeiten", O + P Olhydraulik Und Pneumatik, Vereinigte Fachverlage, Apr. 1, 2005, pp. 218-222, vol. 49, No. 4, Mainz, DE, XP001227255.

Extended European Search Report dated Nov. 19, 2012 (Eight (8) pages).

* cited by examiner

DEVICE FOR DETECTING CONTAMINATION LEVEL OF OPERATING OIL

TECHNICAL FIELD

This invention relates to a contamination level determination system for hydraulic oil, which is installed in a hydraulic working machine such as a construction machine to determine the contamination level of hydraulic oil contaminated with foreign matter that may cause an operation failure of the hydraulic working machine.

BACKGROUND ART

A hydraulic working machine is equipped with a hydraulic circuit that includes hydraulic actuators such as a hydraulic motor and hydraulic cylinders, hydraulic pumps, spool valves or the like, and hydraulic equipment drivable by hydraulic oil. Solid foreign matter is mixed in the hydraulic oil that flows through the hydraulic circuit. There are various kinds of foreign matter including: foreign matter that remains in the hydraulic equipment, piping and a hydraulic oil tank after assembly of the hydraulic circuit (chips from metal working, foundry sand, dust, and the like), foreign matter that is produced inside the hydraulic circuit during operation of the hydraulic circuit (abrasion powder occurring from sliding parts of the hydraulic equipment, sludge occurring as a result of oxidation or degradation of the hydraulic oil, and the like), foreign matter that enters from an external environment into the hydraulic system during operation of the hydraulic circuit, and foreign matter that enters the hydraulic circuit upon maintenance or repair. In particular, foreign matter of substantially the same particle sizes (5 to 50 μm) as the dimensions of clearances in the sliding parts of the hydraulic equipment causes abnormal wear or seizure of the sliding parts and induces an operation failure of the hydraulic working machine.

From such circumstances, it is necessary to perform maintenance of hydraulic oil, such as flushing or replacement, before an operation failure occurs on a hydraulic working machine due to its contamination with foreign matter. For determining whether or not it is a time to perform maintenance, it has conventionally been conducted to determine the level of contamination of hydraulic oil with foreign matter by using a contamination level determination system for hydraulic oil.

Conventional contamination level determination systems are each provided with a light-blocking sensor for sensing foreign matter in hydraulic oil. This light-blocking sensor has a light-emitting section for irradiating laser light onto the hydraulic oil flowing through a line and a light-receiving section for receiving the laser light. These conventional contamination level determination systems are designed to determine the contamination level of hydraulic oil on the basis of a change in the luminous intensity of laser light received at the light-receiving section.

Contamination level determination systems for hydraulic oil, each of which makes use of a light-blocking sensor as described above, involve a potential problem that, when plural pieces of foreign matter exist in laser light at the same time, these plural pieces of foreign matter may be miss-sensed as a large lump of foreign matter. This miss-sensing leads to a reduction in the accuracy of determination of the contamination level of hydraulic oil contaminated with foreign matter of particle sizes that may cause an operation failure.

Contamination level determination systems for hydraulic oil, which are of the above-mentioned type, include those improved in the sensing accuracy of particle sizes of foreign matter by a light-blocking detector of complex construction (see, for example, Patent Document 1).

Patent Document 1: JP-B-3890036

DISCLOSURE OF THE INVENTION

Problem to Be Solved by the Invention

The use of a light-blocking sensor of a complex construction as described above, however, raises another problem in that the manufacturing cost of a contamination level determination system for hydraulic oil increases.

With the foregoing circumstances in view, the present invention has as an object thereof the provision of a contamination level determination system for hydraulic oil, which even with light-blocking sensors of simple construction and low price, can improve the sensing accuracy of a contamination level of hydraulic oil contaminated with foreign matter of particle sizes that may cause an operation failure of a hydraulic working machine.

Means for Solving the Problem

A contamination level determination system of the present invention for hydraulic oil is constructed as will be described next.

[1] To achieve the above-mentioned object, the contamination level determination system of this invention for hydraulic oil is a contamination level determination system for hydraulic oil, said system being adapted to sense, by a light-blocking sensor, foreign matter in hydraulic oil flowing through a hydraulic circuit of a hydraulic working machine and to determine a contamination level of the hydraulic oil by using results of the sensing, comprising a filter arranged in a line of the hydraulic circuit to remove, from the hydraulic oil, foreign matter that may cause an operation failure of the hydraulic working machine, a first light-blocking sensor for sensing passage of foreign matter on an upstream side of the filter, a second light-blocking sensor for sensing passage of foreign matter on a downstream side of the filter, a first frequency determination means for determining a frequency of sensing of foreign matter by the first light-blocking sensor, a second frequency determination means for determining a frequency of sensing of foreign matter by the second light-blocking sensor, and a contamination level determination means for determining a contamination level on the upstream side of the filter on a basis of both results of determination by the first and second, frequency determination means.

According to the contamination level determination system of this invention for hydraulic oil constructed as described above, the contamination level on the upstream side of the filter is determined based on the frequencies of sensing of foreign matter on both the upstream side and downstream side of the filter. Even with light-blocking sensors of simple construction and low price, it is hence possible to improve the sensing accuracy of the contamination level of hydraulic oil contaminated with foreign matter of particle sizes that may cause an operation failure of the hydraulic working machine.

[2] The contamination level determination system of the present invention for hydraulic oil may be characterized in that in the contamination level determination system, the filter is a pilot filter for removing foreign matter from hydraulic oil in a pilot line included in the hydraulic circuit. The hydraulic working machine may become hardly controllable if a sliding part of hydraulic equipment such as a spool valve abnormally wears or is seized in a hydraulic circuit of a pilot control system in the hydraulic working machine. As the opening of the pilot filter, a size that makes it possible to remove foreign matter of particle sizes, which may cause an operation failure, is therefore chosen to surely prevent the hydraulic working machine from becoming hardly controllable. As the filter in the contamination level determination system of the present invention for hydraulic oil makes use of the pilot filter already arranged in the hydraulic circuit, the contamination level determination system for hydraulic oil can be realized at lower cost.

When plural pieces of foreign matter exist in laser light, a light-blocking sensor miss-senses these plural pieces of foreign matter as a large lump of foreign matter. This miss-sensing is harder to occur with a narrower line and a lower flow rate. In the hydraulic circuit of the hydraulic working machine, lines in the hydraulic circuit of the pilot control system are narrower and allow hydraulic oil to flow at a lower flow rate than lines in a hydraulic circuit of a drive system. As the first and second, light-blocking sensors are arranged in the one of the lines of the hydraulic circuit of the pilot control system in the contamination level determination system of the present invention for hydraulic oil, the contamination level determination system of the present invention is easier to determine a contamination level with a higher sensing accuracy than one having the first and second, light-blocking sensors arranged in the hydraulic circuit of the drive system, and can be realized at lower cost than one having, in a hydraulic circuit of a hydraulic excavator, a line arranged exclusively for the light-blocking sensors.

[3] The contamination level determination system of the present invention for hydraulic oil may be characterized in that the contamination level determination system further comprises a flow rate determination means for determining whether or not a delivery flow rate of the pilot line is not higher than a predetermined flow rate, and the contamination level determination means is designed to perform the determination of the contamination level when the flow rate of the pilot line has been determined, by the flow rate determination means, to be not higher than the predetermined flow rate. This construction can stabilize the sensing accuracy of a contamination level.

[4] The contamination level determination system of the present invention for hydraulic oil may be characterized in that the contamination level determination system further comprises a pilot pump included in the hydraulic circuit to feed pressure oil to the pilot line, and a revolution speed sensor for sensing a revolution speed of the pilot pump, and the flow rate determination means comprises a revolution speed determination means for determining whether or not a result of sensing of the revolution speed by the revolution speed sensor is not higher than a predetermined revolution speed. When a fixed displacement hydraulic pump is used as the pilot pump, a delivery flow rate and its corresponding revolution speed of the pilot pump are in a direct proportion. Accordingly, the determination of whether or not the result of sensing of a revolution speed of the pilot pump is not higher than the predetermined revolution speed is the same as the determination of whether or not a delivery flow rate of the pilot pump is not higher than the predetermined flow rate. The contamination level determination system of the present invention for hydraulic oil performs the determination of whether or not a delivery flow rate of the pilot pump is not higher than the predetermined flow rate by performing a determination as to whether or not a corresponding revolution speed of the pilot pump is not higher than the predetermined revolution speed, so that the determination of whether or not the delivery flow rate of the pilot pump is not higher than the predetermined flow rate can be performed with a higher accuracy by a simpler construction than performing the determination by actually measuring the delivery flow rate of the pilot pump.

[5] The contamination level determination system of the present invention for hydraulic oil may be characterized in that the contamination level determination system further comprises an oil temperature sensor for sensing a temperature of the hydraulic oil and an oil temperature determination means for determining whether or not the temperature sensed by the oil temperature sensor is not lower than a predetermined temperature, and the contamination level determination means is designed to perform the determination of a contamination level when the sensed temperature has been determined to be not lower than the predetermined temperature by the oil temperature determination means. At low temperatures, hydraulic oil has a high viscosity so that bubbles are hardly allowed to dissipate. Bubbles are unavoidably sensed by a light-blocking sensor. According to the contamination level determination system of the present invention for hydraulic oil, a contamination level is determined when the temperature of the hydraulic oil is not lower than the predetermined temperature. The contamination level determination system of the present invention for hydraulic oil is hence set such that no determination of a contamination level is performed at low temperatures where bubbles are hardly allowed to dissipate. It is, therefore, possible to avoid a reduction in the sensing accuracy of a contamination level, although such a reduction would otherwise occur due to bubbles.

[6] The contamination level determination system of the present invention for hydraulic oil may be characterized in that the contamination level determination system further comprises a maintenance time arrival determination means for determining whether or not a result of the determination of the contamination level as determined by the contamination level determination means has arrived an upper-limit contamination level set beforehand as a contamination level that requires maintenance, and a maintenance time arrival notification means for notifying that the contamination level is determined to have arrived the upper-limit contamination level by the maintenance time arrival determination means. According to the contamination level determination system of the present invention constructed as described above, a contribution can be made to performing maintenance of hydraulic oil at an appropriate time.

[7] The contamination level determination system of the present invention for hydraulic oil may be characterized in that the contamination level determination system further comprises a contamination progress speed estimation means for comparing contamination levels at different time points to estimate a progress speed of contamination, a maintenance time estimation means for estimating a maintenance time for the hydraulic oil on a basis of the progress speed estimated by the contamination progress speed estimation means, and an estimated maintenance time notification means for notifying a result of the estimation of the maintenance time by the maintenance time estimation means. By the contamination level determination system of the present invention constructed as described above, a contribution can also be made to performing maintenance of hydraulic oil at an appropriate time.

Advantageous Effects of the Invention

According to the present invention, there can be provided a contamination level determination system for hydraulic oil, which even with light-blocking sensors of simple construction and low price, can improve the sensing accuracy of a contamination level of hydraulic oil contaminated with foreign matter of particle sizes that may cause an operation failure of a hydraulic working machine.

BEST MODES FOR CARRYING OUT THE INVENTION

Figure 1:
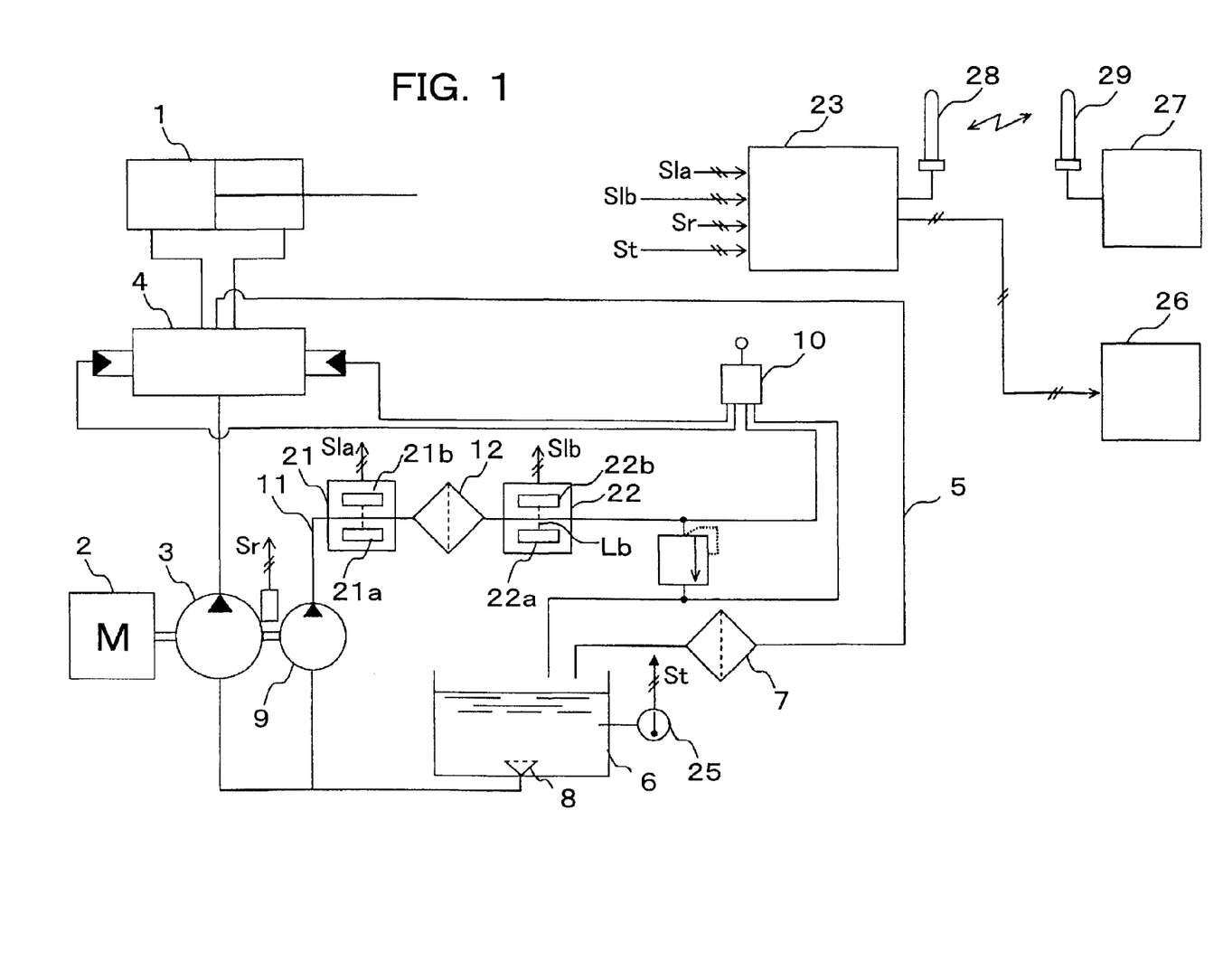
FIG. 1 is a schematic diagram of a hydraulic circuit of a hydraulic working machine equipped with a contamination level determination system according to an embodiment of the present invention for hydraulic oil.
Figure 2:
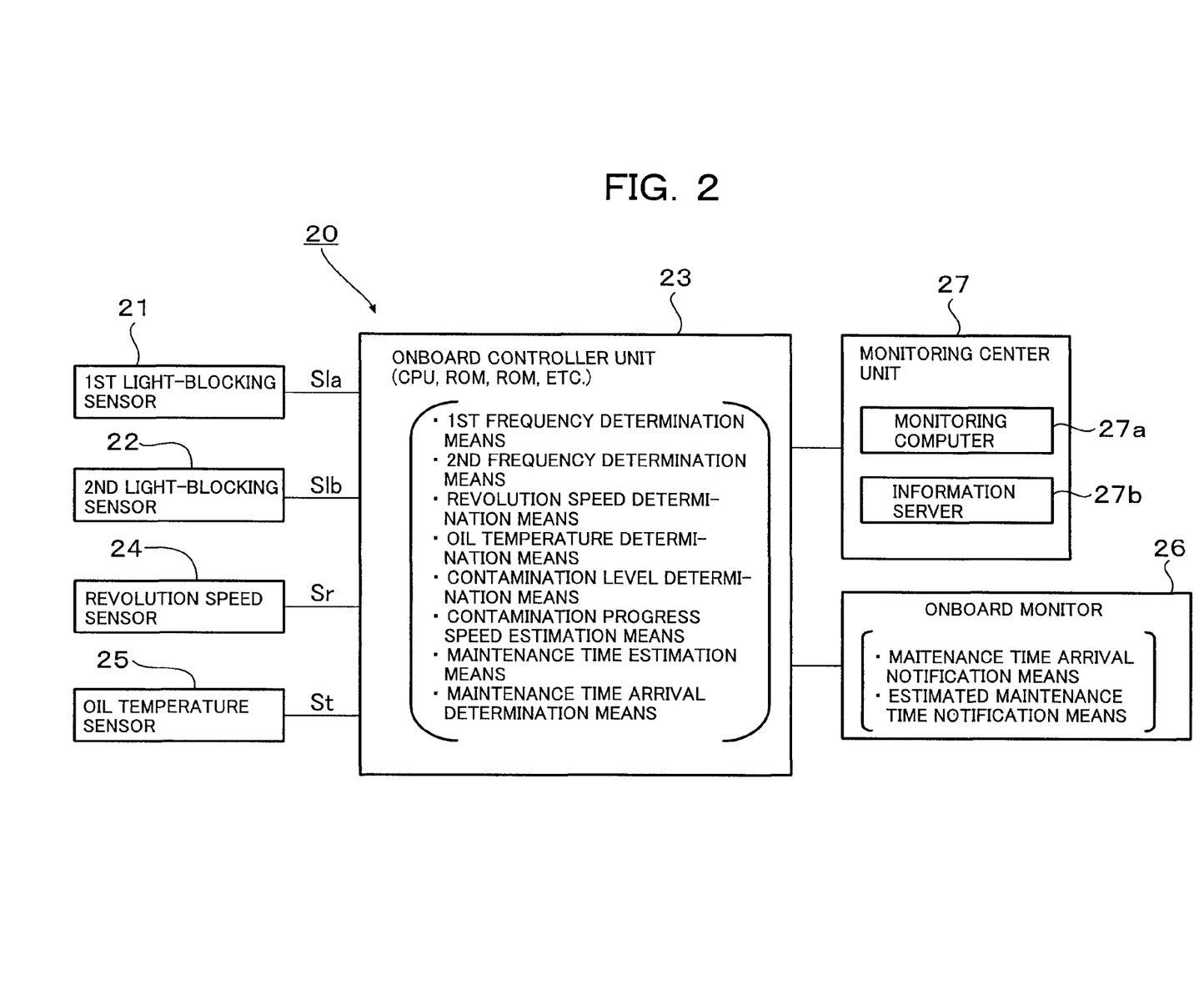
FIG. 2 is a block diagram showing the construction of the contamination level determination system according to the embodiment of the present invention for hydraulic oil.
Figure 3:
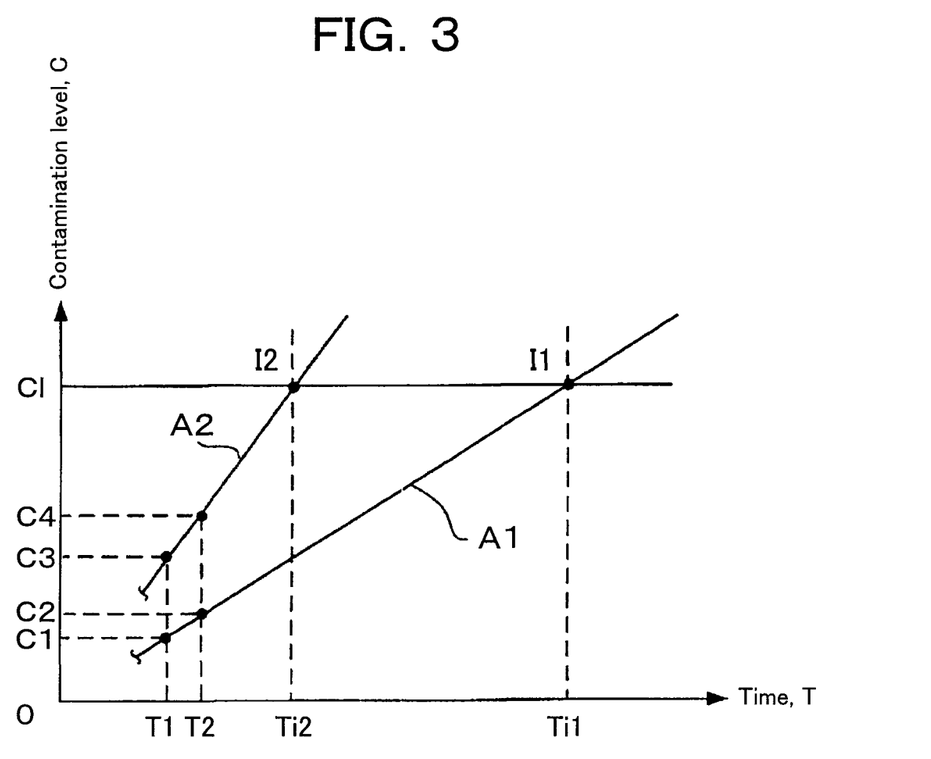
FIG. 3 is a diagram illustrating contamination progress speed functions calculated by the contamination level determination system according to the embodiment of the present invention for hydraulic oil.

A contamination level determination system according to an embodiment of the present invention for hydraulic oil will be described with reference to the drawings. FIG. 1 is a schematic diagram of a hydraulic circuit of a hydraulic working machine equipped with the contamination level determination system according to the embodiment of the present invention for hydraulic oil. FIG. 2 is a block diagram showing the construction of the contamination level determination system according to the embodiment of the present invention for hydraulic oil. FIG. 3 is a diagram illustrating contamination progress speed functions calculated by the contamination level determination system according to the embodiment of the present invention for hydraulic oil.

The hydraulic working machine, for example, a hydraulic excavator is provided with a hydraulic motor as a power source for travel and swing, and also with hydraulic cylinders for driving a front working mechanism. Representing these hydraulic actuators, a hydraulic cylinder 1 is illustrated in FIG. 1. The hydraulic cylinder 1 is driven by pressure oil delivered from a main pump 3 driven by an engine 2 as a power source. A control valve 4 is interposed between the main pump 3 and the hydraulic cylinder 1, and by this control valve 4, a flow of pressure oil to be guided from the main pump 3 into the hydraulic cylinder 1 is controlled. The pressure oil delivered under pressure from the hydraulic cylinder 1 is guided into a hydraulic oil tank 6 via the control valve 4 and a return line 5. The return line 5 and hydraulic oil tank 6 are provided with a return filter 7 (full-flow filter) and a suction filter 8, respectively, to remove foreign matter from the hydraulic oil.

The control valve 4 is a spool valve to which a pilot pressure is applied to switch the same. Using as a primary pressure a delivery pressure of a pilot pump 9 driven by the engine 2 as a power source, this pilot pressure is produced by a pilot valve 10. In a line 11 (pilot line) that guides the primary pressure from the pilot pump 9 into the pilot valve 10, a pilot filter 12 is also arranged to filter the hydraulic oil. If a sliding part of hydraulic equipment such as the control valve 4 (spool valve) in a hydraulic circuit of a pilot control system abnormally wears or is seized, the hydraulic excavator is rendered hardly controllable so that its operator can no longer perform an operation as intended. To ensure the avoidance of occurrence of such a situation, there is chosen, as the opening of the pilot filter, a size capable of removing from the hydraulic oil foreign matter of particle sizes (5 μm to 50 μm) that may cause an operation failure of the hydraulic excavator. It is to be noted that the openings of the return filter 7 and suction filter 8 are of such sizes as causing no interference with a flow of hydraulic oil used at a high flow rate in the hydraulic circuit for the drive system and are greater than the opening of the pilot filter 12.

Especially in the contamination level determination system 20 according to this embodiment, first and second, light-emitting sensors 21,22 are arranged on an upstream size and downstream side of the pilot filter 12, respectively. The first light-emitting sensor 21A has a light-emitting section 21a for irradiating laser light La onto the hydraulic oil flowing through the line 11, and a light-receiving section 21b for receiving the laser light La. When the laser light La irradiated from the light-emitting section 21a is blocked by foreign matter in the hydraulic oil, the luminous intensity of the laser light received at the light-receiving section 21b changes (is reduced) so that the state of the foreign matter is sensed. The laser light La is irradiated in a direction perpendicular to the flow of the hydraulic oil, and the light-receiving section 21b receives the laser light La, converts the luminous intensity of the received laser light La into a luminous intensity signal Sla (electrical signal), and then outputs the signal. The second light-blocking sensor 22 is constructed similar to the first light-blocking sensor 21, and has a light-emitting section 22a for irradiating laser light Lb onto the hydraulic oil flowing through the line 11, and a light-receiving section 22b for receiving the laser light Lb. The light-receiving section 22b receives the laser light Lb, converts the luminous intensity of the received laser light Lb into a luminous intensity signal Slb (electrical signal), and then outputs the signal.

The luminous intensity signals Sla, Slb are inputted into an onboard controller unit 23. This onboard controller unit 23 includes CPU, ROM, RAM, etc., and operates in accordance with a computer program stored beforehand. This onboard controller unit 23 is designed to function as a first frequency determination means for determining, based on the luminous intensity indicated by the luminous intensity signal Sla, a frequency of sensing of foreign matter on the upstream side of the pilot filter 12. The onboard controller unit 23 is also designed to function as a second frequency determination means for determining, based on the luminous intensity indicated by the luminous intensity signal Slb, a frequency of sensing of foreign matter on the downstream side of the pilot filter 12.

Whenever the luminous intensity of laser light La received at the light-receiving section 21b drops to or below a predetermined luminous intensity, the first frequency determination means calculates the particle size of the foreign matter on the basis of the luminous intensity at that time. The first frequency determination means also counts up the number of times that the luminous intensity of the laser light La drops to or below the predetermined luminous intensity within a predetermined time period, whereby the contamination level of the hydraulic oil is determined with respect to every one of preset plural kinds of particle size ranges of foreign matter. Like the first frequency determination means, whenever the luminous intensity of laser light Lb received at the light-receiving section 22b drops to or below the predetermined luminous intensity, the second frequency determination means also calculates the particle size of the foreign matter on the basis of the luminous intensity at that time. The second frequency determination means also counts up the number of times that the luminous intensity of the laser light La drops to or below the predetermined luminous intensity within the predetermined time period, whereby the contamination level of the hydraulic oil is determined with respect to every one of the particle size ranges of foreign matter.

The pilot pump 9 is provided with a revolution speed sensor 24, which senses a revolution speed of the pilot pump 9 and outputs a revolution speed signal Sr (electrical signal) corresponding to the sensed revolution speed. The onboard controller unit 23 is designed to receive the revolution speed signal Sr and to function as a revolution speed determination means for determining whether or not the sensed revolution speed indicated by the revolution speed signal Sr is not higher than a predetermined revolution speed. As the pilot pump 9 is a fixed displacement hydraulic pump, a delivery flow rate and its corresponding revolution speed of the pilot pump 9 are in a direct proportion. Accordingly, the determination of whether or not the result of sensing of a revolution speed by the revolution speed sensor 24 is not higher than the predetermined revolution speed is the same as the determination of whether or not a delivery flow rate of the pilot pump 9 is not higher than the predetermined flow rate. Therefore, the revolution speed determination means constitutes a flow rate determination means for determining whether or not a delivery flow rate of the pilot pump 9 is not higher than the predetermined flow rate. It is to be noted that the term "predetermined revolution speed" means a revolution speed of the pilot pump 9, for example, at the time of low idling of the engine 2.

The hydraulic oil tank 6 is provided with an oil temperature sensor 24, which senses a temperature of the hydraulic oil and outputs an oil temperature signal St (electrical signal) corresponding to the sensed temperature. The onboard controller unit 23 is designed to receive the oil temperature signal St and to function as an oil temperature determination means for determining whether or not the sensed temperature indicated by the oil temperature signal St is not lower than a predetermined temperature.

The onboard controller unit 23 is designed to function as a contamination level determination means for determining a contamination level on the upstream side of the pilot filter 12 on the basis of both results of determination by the first and second frequency determination means. As the opening of the pilot filter 12 is sized to remove, from the hydraulic oil, foreign matter that may cause an operation failure of the hydraulic excavator, foreign matter of the particle size and greater, which may cause an operation failure of the hydraulic excavator, are sensed on the upstream side of the pilot filter 12, and therefore, the frequency of sensing of foreign matter of the particle size and greater on the downstream size is reduced. Further, the frequency of miss-sensing by the first light-blocking sensor 21 and the frequency of miss-sensing by the second light-blocking sensor 22 are substantially the same. For these features, the contamination level determination means can correct any effect of miss-sensing by the first light-blocking sensor 21 on the result of determination of the contamination level by comparing the result of determination of the sensing frequency of foreign matter of particle sizes, which may cause an operation failure of the hydraulic excavator, by the first frequency determination means with the result of determination of the sensing frequency of foreign matter of the same particle sizes by the second frequency determination means upon determining the contamination level on the upstream side of the pilot filter 12.

The contamination level determination means is also designed to perform the determination of a contamination level when a revolution speed of the pilot pump 9 is determined to be not higher than the predetermined revolution speed by the revolution speed determination means and when a sensed temperature is determined to be not lower than the predetermined temperature by the oil temperature determination means.

The onboard controller unit 23 is designed to function as a maintenance time arrival determination means for determining whether or not the result of determination of a contamination level by the contamination level determination means has arrived at an upper-limit contamination level Cl set beforehand as an upper limit of contamination level that requires maintenance. Further, the onboard controller unit 23 is also designed to control an onboard monitor 26 arranged in an operator's cab of the hydraulic excavator and to display on the onboard monitor 26 a screen image indicating that by the maintenance time arrival determination means, the contamination level is determined to have arrived at the upper-limit contamination level. In other words, the onboard controller unit 23 and onboard monitor 26 constitute a maintenance time arrival notification means for notifying that by the maintenance time arrival determination means, the contamination level is determined to have arrived at the upper-limit contamination level.

The onboard controller unit 23 is designed to function as a contamination progress speed estimation means for comparing contamination levels at different time points to estimate a progress speed of contamination, and is also designed to function as a maintenance time estimation means for estimating a maintenance time for the hydraulic oil on the basis of the progress speed estimated by the contamination progress speed estimation means. The onboard controller unit 23 is designed to control the onboard monitor 26, and to display on the onboard monitor 26 a screen image indicating the estimation result of the maintenance time by the maintenance time estimation means. In other words, the onboard controller unit 23 and onboard monitor 26 constitute an estimated maintenance time notification means for notifying the result of estimation of a maintenance time by the maintenance time estimation means.

As illustrated in FIG. 3, the contamination progress speed estimation means calculates a contamination progress speed function A1 [A1=(C2−C1)/(T2−T1)] when the contamination level at a time point T1 and the contamination level at a time point T2 have been determined to be C1 and C2, respectively. The maintenance time estimation means calculates a time point Ti1 available from a crossing I1 of the contamination progress speed function A1 and an upper-limit contamination level Cl, then calculates a time "Ti1−T2" until the time point Ti1 is reached from the time point T1, and further, calculates a maintenance time from the time "Ti1−T2" and the time point T2 at which the contamination level was determined.

The contamination progress speed function A1 is one example of those obtained at the time of quarry work by the hydraulic excavator, and the contamination progress speed function is not limited to the contamination progress speed function A1 and differs depending on the environment and work details at a work site of the hydraulic excavator. A contamination progress speed function A2 [=(C4−C3)/(T2−T1)] shown in FIG. 3 is one example of those obtained at the time of crushing work performed by providing the hydraulic excavator with a breaker in place of a bucket. At a site of crushing work, a great deal of dust is flying around, and a breaker performs as many reciprocations as several hundreds times per minute in such a dusty environment. Therefore, dust (foreign matter) tends to enter from between a cylinder tube and a piston rod in a hydraulic cylinder that drives the breaker, and the interval between a time point Ti2, which is available from a crossing I2 of the contamination progress speed function A2 and the upper-limit contamination level Cl, and the time point T2 becomes shorter than the interval between the above-mentioned time point Ti1 and the time point T2. In other words, the maintenance time interval for hydraulic oil becomes shorter in crushing work than in quarry work. Earlier maintenance also becomes necessary when a trouble occurs on the hydraulic equipment mounted on the hydraulic excavator and the production of abrasion powder increases.

The onboard controller unit 23 is communicably connected to a monitoring center unit 27 via antennas 28,29. The monitoring center unit 27 is provided with a monitoring computer 27a for preparing data for the monitoring of conditions of the hydraulic excavator and an information server 27b for accumulating various data of the hydraulic excavator as transmitted from the onboard controller unit 23 and data prepared by the monitoring computer 27a. The above-described various data include the result of sensing by the first light-blocking sensor, the result of sensing by the second light-blocking sensor, the result of sensing by the revolution speed sensor, the result of sensing by the oil temperature sensor, the results of determination by the first frequency determination means, the results of determination by the second frequency determination means, the result of determination by the revolution speed determination means, the result of determination by the oil temperature determination means, the result of determination by the contamination level determination means, the result of estimation by the contamination progress speed estimation means, the result of estimation by the maintenance time estimation means, and the result of determination by the maintenance time arrival determination means. The monitoring computer 27a can perform a detailed analysis on the contamination level of the working oil by using the data from the onboard controller unit 23. On the other hand, the monitoring center unit 27 informs a customer of a contamination progress speed, an estimated maintenance time, the arrival of a contamination level of the hydraulic oil at the upper-limit contamination level Cl, and the like through a communication line.

According to the contamination level determination system 20 of this embodiment, the following advantageous effects can be brought about.

The contamination level determination system 20 determines the contamination level on the upstream side of the pilot filter 12 on the basis of the frequencies of sensing of foreign matter on both the upstream side and downstream side of the pilot filter 12. Even with light-blocking sensors of simple construction and low price, it is hence possible to improve the sensing accuracy of the contamination level of hydraulic oil contaminated with foreign matter of particle sizes that may cause an operation failure of the hydraulic excavator.

In the contamination level determination system 20, the arrangement locations of the first and second, light-blocking sensors 21,22 are on the upstream side and downstream side of the pilot filter, respectively. Therefore, the contamination level determination system 20 makes use of the pilot filter already arranged in the hydraulic circuit of the hydraulic excavator, and can be realized at lower cost.

When plural pieces of foreign matter exist in the laser light La or Lb at the same time, the first light-blocking sensor 21 or second light-blocking sensor 22 miss-senses these plural pieces of foreign matter as a large lump of foreign matter. This miss-sensing is harder to occur with a narrower line and a lower flow rate. In the hydraulic circuit of the hydraulic excavator, the lines in the hydraulic circuit of the pilot control system are narrower and allow hydraulic oil to flow at a lower flow rate than the lines in the hydraulic circuit of the drive system. In the contamination level determination system 20, the first and second, light-blocking sensors 21,22 are arranged in the line 11 of the hydraulic circuit of the pilot control system. Therefore, the contamination level determination system 20 is easier to determine a contamination level with a higher sensing accuracy than one having the first and second, light-blocking sensors 21,22 arranged in the hydraulic circuit of the drive system, and can be realized at lower cost than one having, in the hydraulic circuit of the hydraulic excavator, a line arranged exclusively for the sensors.

The contamination level determination system 20 is provided with the flow rate determination means for determining whether or not a delivery flow rate of the pilot pump is not higher than the predetermined flow rate, and is designed to perform the determination of a contamination level when a delivery flow rate of the pilot pump 9 has been determined, by the flow rate determination means, to be not higher than the predetermined flow rate. This construction can stabilize the sensing accuracy of a contamination level. Further, the accuracies of sensing of foreign matter by the first and second, light-blocking sensors 21,22 can each be stabilized at a high level because the predetermined flow rate is the flow rate of the pilot pump 9 at the time of low idling of the engine 2.

The contamination level determination system 20 performs the determination of whether a delivery flow rate of the pilot pump 9 is not higher than the predetermined flow rate by performing a determination as to whether or not a corresponding revolution speed of the pilot pump 9 is not higher than the predetermined revolution speed. Therefore, the determination of whether or not the delivery flow rate of the pilot pump 9 is not higher than the predetermined flow rate can be performed with a higher accuracy by a simpler construction than performing the determination from an actual measurement value of the delivery flow rate of the pilot pump 9.

In the contamination level determination system 20, the contamination level determination means is designed to perform the determination of a contamination level when a temperature sensed by the oil temperature sensor 24 has been determined to be not lower than the predetermined temperature by the oil temperature determination means. At low temperatures, hydraulic oil has a high viscosity so that bubbles are hardly allowed to dissipate. Bubbles are unavoidably sensed by the first and second, light-blocking sensors 21,22. As the contamination level determination system 20 determines the contamination level when the temperature of the hydraulic oil is not lower than the predetermined temperature, the contamination level determination system 20 can be set such that no determination of a contamination level is performed at low temperatures where bubbles are hardly allowed to dissipate. As a consequence, it is possible to reduce the frequencies of sensing of bubbles by the first and second, light-blocking sensors 21,22, and therefore, to avoid a reduction in the sensing accuracy of a contamination level although such a reduction would otherwise occur due to bubbles.

The contamination level determination system 20 notifies the arrival of the contamination level of the hydraulic oil at the upper-limit contamination level Cl and the estimated maintenance time by means of the onboard monitor 26. A contribution can, therefore, be made to performing maintenance of hydraulic oil at an appropriate time.

In the above-mentioned embodiment, the onboard controller unit 23 is designed to function as the first frequency determination means, the second frequency determination means, the revolution speed determination means, the oil temperature determination means, the contamination level determination means, the contamination progress speed estimation means, the maintenance time estimation means, and the maintenance time arrival determination means. However, these means in the present invention are not limited to those functioned by the onboard controller unit 23, and the contamination level determination system 20 may be set such that some or all of these functions are performed by the monitoring center unit 27.

In the above-mentioned embodiment, the result of sensing by the revolution speed sensor 24 is used to determine whether or not a revolution speed of the pilot pump 9 is not higher than the predetermined revolution speed. The present invention is, however, not limited to such an embodiment. The contamination level determination system 20 may be designed to use the result of sensing by a revolution speed sensor, which senses a revolution speed of the engine 2, or a command value of revolution speed for the engine 2 in place of the revolution speed sensor 24 and to indirectly determine whether or not a revolution speed of the pilot pump 9 is not higher than the predetermined revolution speed.

In the above-mentioned embodiment, the first and second, light-blocking sensors 21, 22, which use laser light, are used as the first and second, light-blocking sensors for sensing foreign matter. In the present invention, however, the first and second, light-blocking sensors are not limited to those using laser light, and conventional light-blocking sensors which use light may be employed.

LEGEND

1 Hydraulic cylinder
2 Engine
3 Main pump
4 Control valve
5 Return line
6 Hydraulic oil tank
7 Return filter
8 Suction filter
9 Pilot pump
10 Pilot valve
11 Line
12 Pilot filter
20 Contamination level determination system
21 First light-blocking sensor
21a Light-emitting section
21b Light-receiving section
22 Second light-blocking sensor
22a Light-emitting section
22b Light-receiving section
23 Onboard controller unit
24 Revolution speed sensor
25 Oil temperature sensor
26 Onboard monitor
27 Monitoring center unit
27a Monitoring computer
27b Information server
28 Antenna
29 Antenna

The invention claimed is:

1. A contamination level determination system for hydraulic oil, said system being adapted to sense, by a light-blocking sensor, foreign matter in hydraulic oil flowing through a hydraulic circuit of a hydraulic working machine and to determine a contamination level of the hydraulic oil by using results of the sensing, comprising:
a filter arranged in a line of the hydraulic circuit to remove, from the hydraulic oil, foreign matter that may cause an operation failure of the hydraulic working machine,
a first light-blocking sensor for sensing passage of foreign matter on an upstream side of the filter,
a second light-blocking sensor for sensing passage of foreign matter on a downstream side of the filter,
a first frequency determination means for determining a frequency of sensing of foreign matter on the upstream side of the filter by the first light-blocking sensor,
a second frequency determination means for determining a frequency of sensing of foreign matter on the downstream side of the filter by the second light-blocking sensor, and
a contamination level determination means for correcting an effect of miss-sensing on the first light-blocking sensor by comparing a result of determination of the first frequency determination means with a result of determination of the second frequency determination means,
a contamination progress speed estimation means for comparing contamination levels at different time points to estimate a progress speed of contamination,
a maintenance time estimation means for estimating a maintenance time for the hydraulic oil on a basis of the progress speed estimated by the contamination progress speed estimation means, and
an estimated maintenance time notification means for notifying a result of estimation of the maintenance time by the maintenance time estimation means.

2. The contamination level determination system according to claim 1, wherein:
the filter is a pilot filter for removing foreign matter from hydraulic oil in a pilot line included in the hydraulic circuit.

3. The contamination level determination system according to claim 2, further comprising:
a flow rate determination means for determining whether or not a delivery flow rate of the pilot line is not higher than a predetermined flow rate,
wherein the contamination level determination means is designed to perform the determination of the contamination level when the flow rate of the pilot line has been determined, by the flow rate determination means, to be not higher than the predetermined flow rate.

4. The contamination level determination system according to claim 3, further comprising:
a pilot pump included in the hydraulic circuit to feed pressure oil to the pilot line, and
a revolution speed sensor for sensing a revolution speed of the pilot pump,
wherein the flow rate determination means comprises a revolution speed determination means for determining whether or not a result of sensing of the revolution speed by the revolution speed sensor is not higher than a predetermined revolution speed.

5. The contamination level determination system according to claim 1, further comprising:
an oil temperature sensor for sensing a temperature of the hydraulic oil, and an oil temperature determination means for determining whether or not the temperature sensed by the oil temperature sensor is not lower than a predetermined temperature,
wherein the contamination level determination means is designed to perform the determination of a contamination level when the sensed temperature has been determined to be not lower than the predetermined temperature by the oil temperature determination means.

6. The contamination level determination system according to claim 1, further comprising:
- a maintenance time arrival determination means for determining whether or not a result of the determination of the contamination level as determined by the contamination level determination means has arrived at an upper-limit contamination level set beforehand as a contamination level that requires maintenance, and
- a maintenance time arrival notification means for notifying that the contamination level is determined to have arrived the upper-limit contamination level by the maintenance time arrival determination means.

* * * * *